United States Patent
Itagi

(10) Patent No.: US 10,613,039 B2
(45) Date of Patent: *Apr. 7, 2020

(54) MICROWAVE MOISTURE METER AND SENSOR

(71) Applicant: TSI, Incorporated, Shoreview, MN (US)

(72) Inventor: Amit Vasant Itagi, Ellicott City, MD (US)

(73) Assignee: TSI, INCORPORATED, Shoreview, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/154,195

(22) Filed: Oct. 8, 2018

(65) Prior Publication Data

US 2019/0170664 A1 Jun. 6, 2019

Related U.S. Application Data

(63) Continuation of application No. 15/503,978, filed as application No. PCT/US2015/044800 on Aug. 12, 2015, now Pat. No. 10,094,789.

(Continued)

(51) Int. Cl.
*G01N 22/04* (2006.01)
*G01N 24/08* (2006.01)
(Continued)

(52) U.S. Cl.
CPC ........... *G01N 22/04* (2013.01); *G01N 24/081* (2013.01); *G01N 33/025* (2013.01); *G01N 22/00* (2013.01);
(Continued)

(58) Field of Classification Search
CPC ........ G01N 22/00; G01N 22/04; G01N 24/00; G01N 24/08; G01N 24/081; G01N 33/00;
(Continued)

(56) References Cited

U.S. PATENT DOCUMENTS 3,818,333 A 6/1974 Walker
4,257,001 A 3/1981 Partain et al.
(Continued)

FOREIGN PATENT DOCUMENTS

EP 0806654 A2 12/1997
EP 1573305 A2 9/2005
(Continued)

OTHER PUBLICATIONS

Extended European Search Report for EP Application No. 1532114. 1, dated Dec. 12, 2017, 10 pages.
(Continued)

*Primary Examiner* — Hoai-An D. Nguyen
(74) *Attorney, Agent, or Firm* — Kagan Builders, PLLC

(57) ABSTRACT

A microwave moisture sensor for agricultural materials, such as grains and nuts, is disclosed herein that includes a material sample holder having a substantially cylindrical cavity formed therein. The meter assembly further includes a transmitting antenna on a side of the sample holder and a receiving antenna on a side of sample holder directly opposite the transmitting antenna wherein the sample holder is located between the two antennas, the receiving antenna configured to receive a transmitted microwave through the sample holder.

19 Claims, 4 Drawing Sheets

(CYLINDRICAL SAMPLE HOLDER WITH A MATCHING BOX)

Related U.S. Application Data

(60) Provisional application No. 62/037,184, filed on Aug. 14, 2014.

(51) Int. Cl.
    *G01N 33/02* (2006.01)
    *G01N 33/00* (2006.01)
    *G01N 22/00* (2006.01)
    *G01N 24/00* (2006.01)

(52) U.S. Cl.
    CPC ............. *G01N 24/00* (2013.01); *G01N 24/08* (2013.01); *G01N 33/0098* (2013.01)

(58) Field of Classification Search
    CPC ... G01N 33/02; G01N 33/025; G01N 33/0098
    USPC ....... 324/600, 629, 633, 634, 637, 639, 640, 324/642, 643, 76.11, 96; 73/73
    See application file for complete search history.

(56) References Cited

U.S. PATENT DOCUMENTS

| | | | |
|---|---|---|---|
| 4,319,185 A | 3/1982 | Hill | |
| 4,813,270 A * | 3/1989 | Baillie | G01F 1/74 374/33 |
| 5,006,785 A * | 4/1991 | Revus | G01N 22/00 250/301 |
| 5,030,476 A | 7/1991 | Okamura et al. | |
| 5,333,493 A | 8/1994 | Cutmore | |
| 5,413,631 A | 5/1995 | Gray et al. | |
| 5,581,191 A | 12/1996 | Yamaguchi | |
| 5,621,330 A | 4/1997 | Greenwald et al. | |
| 6,147,503 A | 11/2000 | Nelson et al. | |
| 6,435,130 B1 | 8/2002 | Takaki et al. | |
| 6,691,563 B1 | 2/2004 | Trabelsi et al. | |
| 7,143,638 B1 | 12/2006 | Scott | |
| 8,629,681 B1 | 1/2014 | Trabelsi et al. | |
| 10,094,789 B2 * | 10/2018 | Itagi | G01N 22/04 |

FOREIGN PATENT DOCUMENTS

| | | |
|---|---|---|
| KR | 20140082376 A | 7/2014 |
| WO | 2000/014552 A1 | 3/2000 |
| WO | 2009/063497 A2 | 5/2009 |

OTHER PUBLICATIONS

International Search Report and Written Opinion for International Application No. PCT/US2015/044800, dated Feb. 23, 2016 (11 pages).

* cited by examiner

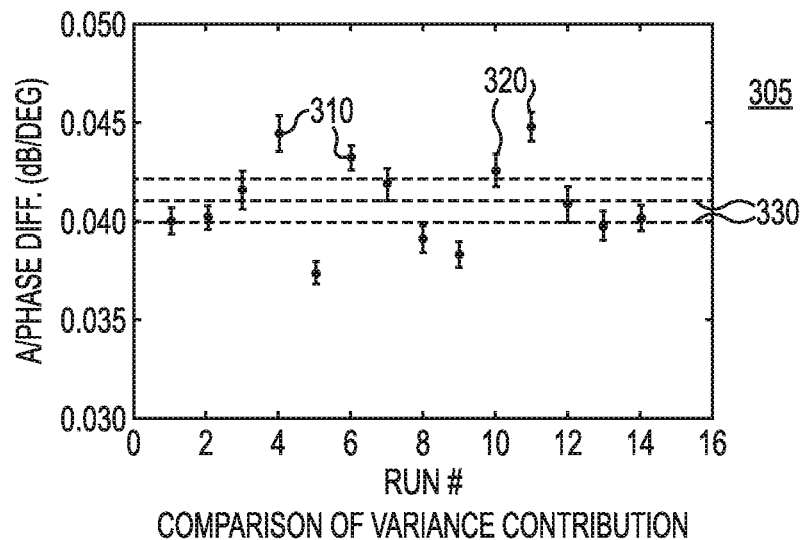
Fig. 3
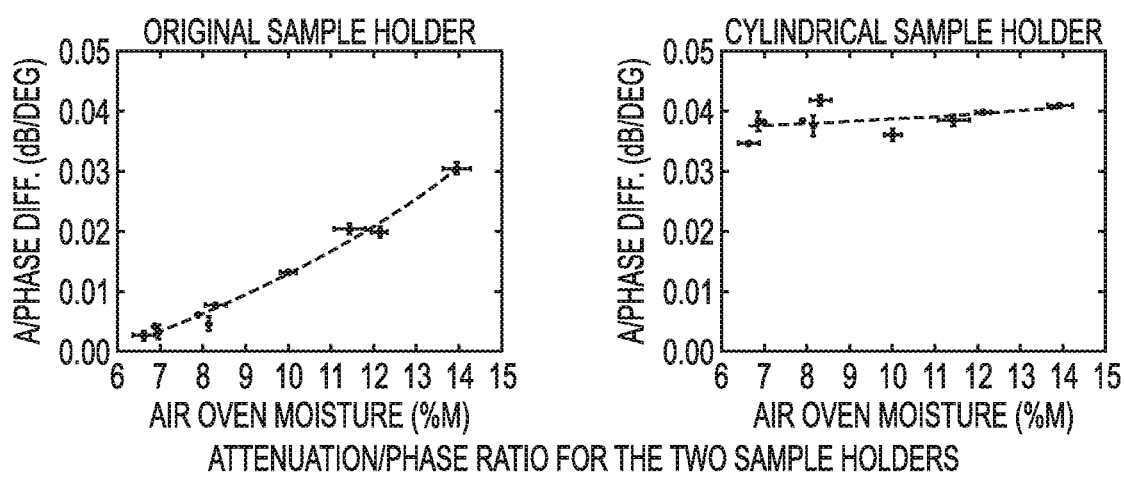
Fig. 4A
(RECTANGULAR)
Fig. 4B
(CYLINDRICAL)

(CYLINDRICAL SAMPLE HOLDER WITH A MATCHING BOX)

(ATTENUATION/PHASE RATIO AS A FUNCTION OF THE PEANUT MOISTURE FOR THE MATCHING BOX GEOMETRY)

LINEAR POLARIZATION

CIRCULAR POLARIZATION

MICROWAVE MOISTURE METER AND SENSOR

CLAIM OF PRIORITY

This application is a continuation of U.S. application Ser. No. 15/503,978, now U.S. Pat. No. 10,094,789, which claims priority to International Application No. PCT/US2015/044800, filed on Aug. 12, 2015, which claims priority to and the benefit of U.S. provisional application No. 62/037,184, filed on Aug. 14, 2014, the entire disclosures of which are incorporated by reference for all purposes.

FIELD AND BACKGROUND OF THE INVENTION

The invention generally relates to microwave sensors for detecting moisture content in agricultural materials.

Moisture content of materials is a key parameter in many research and industrial applications, including the food and agriculture-related industries. The most widely used standard techniques for moisture content determination are various forms of oven drying. These techniques are based on drying samples under specific conditions, such as temperature and time, depending on the material. Besides being energy and time consuming, in some instances the representative character of the samples might be questionable compared to the whole volume or mass of material under consideration. Moreover, most industrial processes are highly automated and require real-time, on-line measurement of the moisture content.

For grains, moisture is an important factor affecting price paid for grain. Therefore, moisture content must be determined whenever grain is traded. If moisture content is too high at the time of harvest, the grain kernels can be damaged in the mechanical harvesting process, leaving them more susceptible to infection by fungi. If they are stored at moisture contents too high for the prevailing environment, they can spoil because of the action of microorganisms, and the value is degraded or completely lost for human and animal consumption. Electrical measurement methods have been developed that depend on correlations between the electrical properties of the grain and moisture content and grain moisture meters in the United States today are predominantly those operating at about 149 MHz and that sense the dielectric properties (relative permittivity) of the grain samples.

Research on sensing moisture content in grain by microwave measurements has indicated two important advantages for microwave frequencies. The inconsistency of moisture measurements by instruments operating in the low frequency range may be due, in part, to the influence of ionic conduction on the measured dielectric properties at high moisture levels. At microwave frequencies, the influence of ionic conduction is negligible, and better correlations between permittivity and moisture content can be expected.

In U.S. Pat. No. 8,629,681, Trabelsi et al provide a method that appeared to solve some of the problems associated with the measurement of density and moisture content of bulk materials. FIG. 1 shows part of the basic concept of the microwave measurement system 10 proposed by Trabelsi et al, which includes a rectangular sample holder 20 that is placed between two directional antennas. One antenna acts as a transmit (Tx) antenna 30 and the other acts as a receive (Rx) antenna 40. The phase and attenuation of the microwave beam as it traverses sample holder 20 is measured with and without peanuts in sample holder 20. Trabelsi et al appear to teach that a relative change in the phase and attenuation of the microwave beam that traverses sample holder 20 is used to estimate the moisture content of the peanuts. A correction is then applied to correct for the temperature of the peanut sample.

During the testing of the Trabelsi '681 moisture meter prototype in a grain lab, it was discovered that the moisture meter provided adequate results, however the levels of accuracy and repeatability of results demanded by users in the market are higher. Hence there is a need in the market for a microwave-based moisture meter system exhibiting higher levels of measurement accuracy with consistent repeatability of outcomes.

SUMMARY

A closer analysis of the prior art microwave moisture meter revealed the sources of variations that limit the accuracy and repeatability of outcomes. In an example embodiment, a microwave moisture meter assembly including a microwave source is configured to measure attenuation and phase changes in a measured material. The microwave moisture meter assembly includes a material sample holder assembly having a cavity formed therein, in this example the cavity being a substantially cylindrical cavity, with a longitudinal axis through a length of the cavity and the holder assembly. The meter assembly further includes a transmitting antenna on a side of the sample holder and a receiving antenna on an opposite side of sample holder directly opposite the transmitting antenna, the receiving antenna configured to receive a transmitted circular polarized microwave through the sample holder, wherein the sample holder is comprised of a material that approximates a permittivity of a material being measured that is disposed within the sample holder. In a related embodiment, the meter assembly further includes a rotator mechanism operatively in contact with and configured to rotate the material sample holder assembly. In another related embodiment, the sample holder assembly includes a cylindrically shaped holder removably housed within the cavity of the material sample holder assembly that is configured to be rotatable within the sample holder assembly. In yet another related embodiment, wherein the inner holder member or the material sample holder assembly, or both, are comprised of material having a permittivity selected to be in a midrange of a percent moisture content of the individual particles of the sampled material.

In another example embodiment, a microwave moisture meter assembly including a microwave source, the microwave meter assembly configured to measure attenuation and phase changes in a sample of material being measured, the microwave meter assembly including a material sample holder assembly having a substantially inner cylindrical holder member disposed within an outer holder member, the inner cylindrical holder member having a longitudinal axis along a length of the cylindrical holder and configured to be rotated axially about the longitudinal axis within the outer holder member, wherein the outer holder member is comprised of a material that approximates a permittivity of the sample material being measured within the sample holder assembly. The meter assembly includes a rotator mechanism in operative contact with the inner holder and configured to at least axially rotate the inner cylindrical holder within the outer holder member. The meter assembly also includes a pair of antennas, a transmitting antenna located on a side of the material sample holder configured to transmit a polarized microwave signal, and a receiving antenna located on a side of the material sample holder assembly directly opposite the transmitting antenna such that the material sample holder is located in between both antennas, the receiving antenna configured to receive the microwave signal transmitted through the sample holder. In this example embodiment, the mode of polarization of the microwave signal is circular. In yet other related embodiments, the mode of polarization is linear (in either the horizontal or vertical direction) or elliptical.

In a related embodiment, the cylindrically shaped sample holder and the antennas are substantially similar in height while the outer holder is configured substantially in the shape of a block configured to receive and support the cylindrically shaped holder between the transmitting and receiving antennas. In another embodiment, the permittivity of the inner and outer holder members is selected to be in a midrange of a percent moisture content of the individual particles of the sampled material.

In another example embodiment, a microwave moisture meter assembly including a microwave source, the microwave meter assembly configured to measure attenuation and phase changes in a sample of material being measured, the microwave meter assembly including a material sample holder assembly including a holder member having a longitudinal axis along a length of the holder member. In addition, a rotator mechanism is in operative contact with the holder member and is configured to axially rotate the holder member. The meter assembly includes two antennas, a transmitting antenna located on a side of the material sample holder assembly and configured to transmit a polarized microwave signal, and a receiving antenna located on a side of the material sample holder assembly directly opposite the transmitting antenna such that the material sample holder assembly is located in between both antennas, the receiving antenna configured to receive the microwave signal transmitted through the sample holder. In one example embodiment, the meter assembly further includes an outer holder member disposed outside and about the holder member, wherein the outer holder member is comprised of a material that approximates a permittivity of the sample material being measured within the sample holder assembly. In a related example embodiment, the holder member of the meter assembly is configured as a substantially cylindrical holder member capable of rotating axially within the outer holder member. In various embodiments, the meter assembly operates in various modes including linear polarization (either the horizontal or vertical direction) or elliptical.

In related example embodiments, the aforementioned microwave moisture meter assembly detects the moisture content of an object (such as a peanut, grain or seed) using linear or circular polarization wave propagation through the object being measured.

BRIEF DESCRIPTION OF THE DRAWINGS

Other important objects and advantages of the present invention will be apparent from the following detailed description of the invention taken in connection with the accompanying drawings in which:

FIG. 3 is a graph that illustrates a comparison of variance contributions from different sources;

FIGS. 4A and 4B are graphs that illustrate a comparison for two moisture meter configurations of attenuation/phase ratios accordance with the invention;

DETAILED DESCRIPTION OF THE INVENTION

Following below are more detailed descriptions of various embodiments of an improved microwave moisture meters or sensors and systems described herein. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

In most of the embodiments described herein, we relied on the microwave moisture meter arrangement (FIG. 1) described in U.S. Pat. No. 8,629,681, the disclosure of which is incorporated by reference in its entirety, and focus most of the discussion herein on the sample holder and antenna arrangements and the variations in the moisture meter signal.

Figure 2:
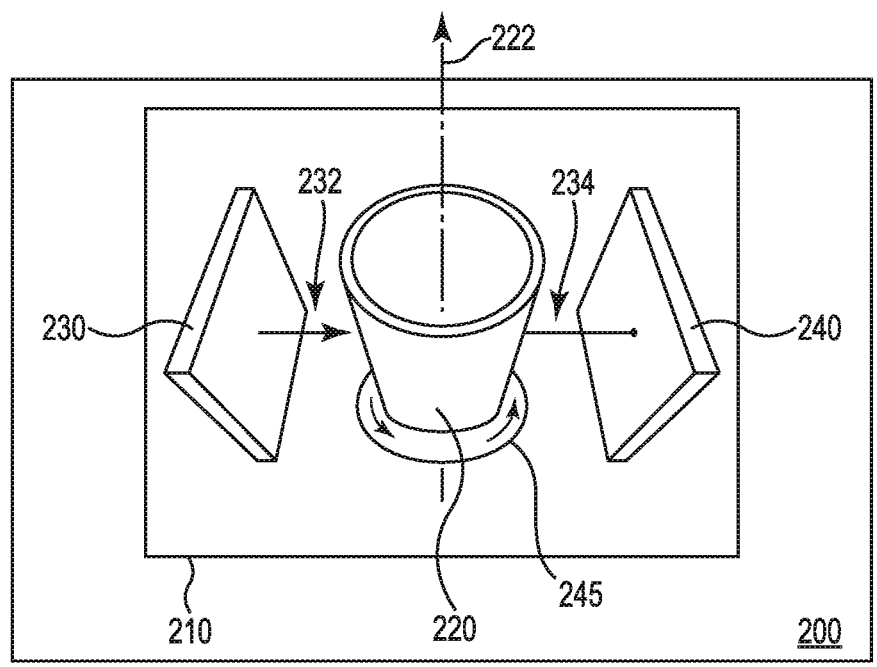
FIG. 2 illustrates a microwave moisture meter configuration in accordance with the invention.
Figure 7:
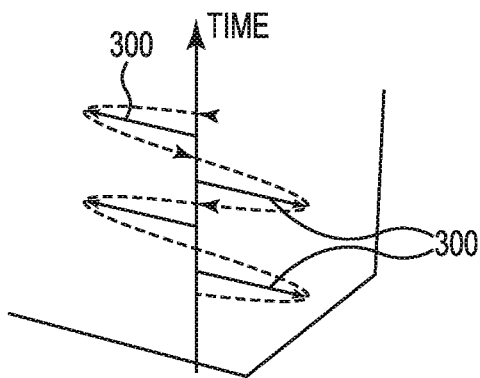
FIG. 7 is a graph that illustrates linear polarization in accordance with the invention.

Referring now to the figures, in FIGS. 2 and 7, there is illustrated a sample material holder assembly and antenna configuration 210 of a microwave moisture meter 200 (not shown) that includes a cylindrical sample holder 220 bounded by a transmitting antenna 230 on one side and a receiving antenna 240. In this example embodiment, sample holder 220 includes a longitudinal axis 222 along a length of holder 220 and is rotated axially in either direction by a rotator mechanism, represented by disk or platen 245 (arrows, right circular direction in this example). A polarized microwave signal 232 originates from transmitting antenna 230, passes through holder 220 and the sampled material and is received by receiving antenna 240 as an attenuated wave 234 (which may also exhibit a phase difference as well depending upon the amount of moisture in the sampled material) in holder 220. In this and other example embodiments, platen 245 rotates in either direction, at any speed (since the microwave signals travel so quickly and measurements occur rapidly) and at any speed, which assists in removing variations in measurements that may be caused by the alignment of the individual particles of the sampled material.

In this and most of the following embodiments, the mode of operation will be linear polarization of the microwave propagation, which is illustrated in FIG. 7, in either the vertical or horizontal direction or orientation. With linear propagation, various arrows 300 show the electric field direction at a point in space as a function of time as created by the transmitting antenna, which causes the field to oscillate linearly along a plane normal to the direction of wave propagation. The receiving antenna is reciprocally sensitive to the linear polarization.

In this example embodiment, the microwave frequency used for this measurement is about 5.8 GHz and the measurements are taken using peanuts. The real part of the peanut dielectric constant is around 2, however the exact value changes with moisture (in one example, moisture can range from about 8% to about 20%). In a medium of dielectric constant of about 2, the microwave wavelength is around 3.6 cm. This is comparable to the length/diameter of a peanut pod. Thus, the microwaves do not see the peanuts either as scattering points or as a homogeneous medium. The microwave attenuation/phase therefore will have some variation depending on the physical configuration of the peanuts in the sample holder. Experimentally, it has been seen that this variation is a big contributor to the overall variance of the attenuation and phase measurements in standard rectangular sample holders, which the invention described herein will overcome based on a number of factors.

Figure 1:
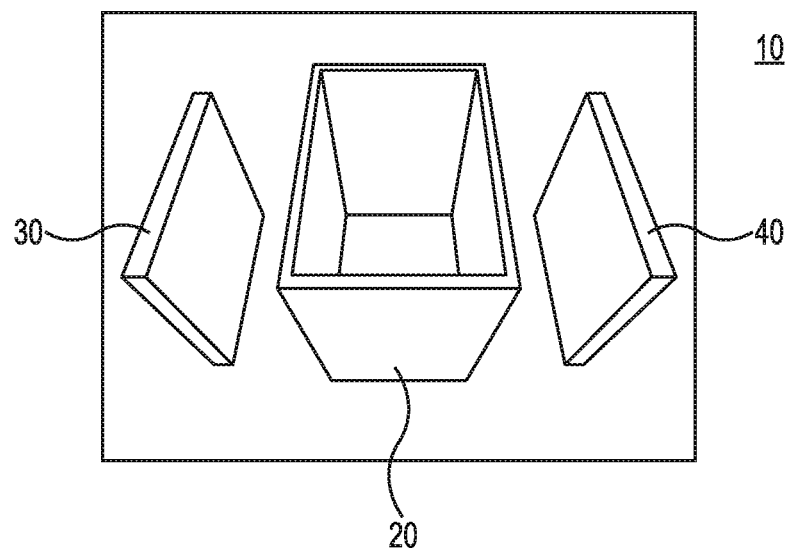
FIG. 1 is a prior art arrangement for a microwave moisture sensor.

In this example embodiment, the sample holder shape is changed from the rectangular bin in FIG. 1 (prior art) to a cylindrically shaped bin or holder 220. Other shapes for the holder can be used as long as they can be axially rotated during moisture measurement. In a related embodiment, a matching block (see FIG. 5) is included about the cylinder bin. In this example embodiment, sample holder 220 is rotated and the average is taken of the data collected over the different angular positions of sample holder 220.

Referring now to FIG. 3, there is shown a graph 305 that illustrates the attenuation/phase ratio for multiple peanut runs/drops, which is basically a comparison of variance contribution to the measurement outcomes. A drop refers to a draw or removal of a peanut sample from the peanut population. Points or dots 310 and the error bars 320 show the average over the angular position and the variation over the angular positions, respectively. The dashed lines 330 represent the variation between points 310 from the different runs. In this plot 305, the error bars represent a 95% confidence interval for the mean. It can be seen that the variation over the angular positions is comparable to the variation over multiple drops. Thus, reducing the first contribution to the variance reduces the total variance considerably.

Although arrangement 210 is an improvement over the prior art, using cylindrical sample holder 220 presents a challenge with respect to some of the measurements. The peanuts have a permittivity of (about) ~2. Thus, a cylindrical mass, such as cylindrical holder 220, can act as a cylindrical lens. The "lens" focuses the microwave beam from the transmitting antenna to a smaller size as it reaches the receiving antenna. This causes a loss in sensitivity at receiving antenna 240, which is illustrated FIG. 4B versus the rectangular holder shown in FIG. 1 (FIG. 4A is the rectangular holder). The attenuation/phase ratio is plotted for the two sample holders as a function of the peanut moisture measured with an air oven. The X-axes in FIGS. 4A, 4B, and 6 show the air oven moisture, which is the moisture in the sample measured independent of the moisture meter when drying the sampled material in an air oven.

Figure 5:
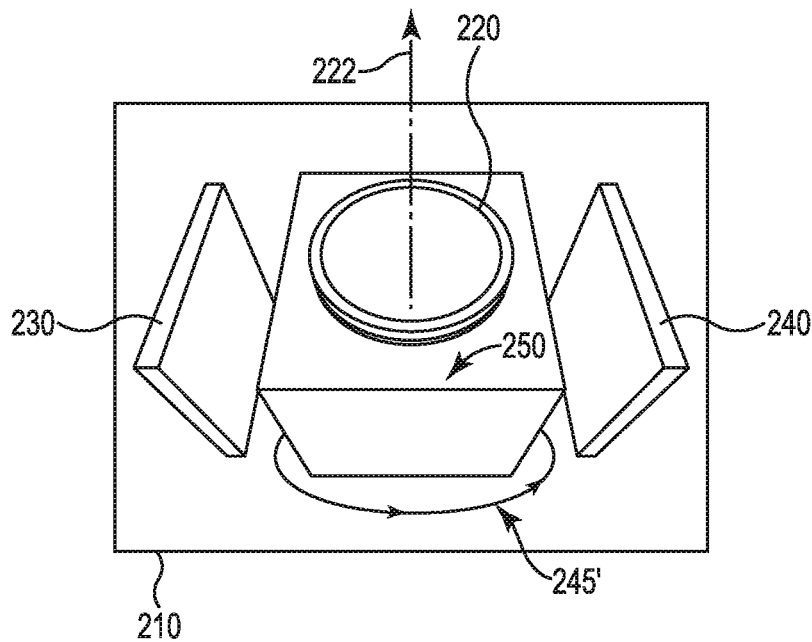
FIG. 5 illustrates another microwave moisture meter configuration in accordance with the invention.

Referring now to FIG. 5, in order to mitigate this loss in sensitivity due to the lensing effect, sample holder (or inner holder member) arrangement 210 is reconfigured so as to use a rectangular block 250 (or any other shape) disposed about and around cylindrical sample holder 220. In this example embodiment, holder 220 is configured to be rotated by a rotator 245' (not shown, only arrow of rotating direction with respect to axis 222) separate from block or outer holder member 250. In this example embodiment, the material of the rectangular block 250 has a permittivity in the range of about 2-3. For the transmitted polarized microwave signals, the matching block appears as an approximate continuation of the cylindrical peanut mass (or whatever material is being measured). The permittivity material matching as well as the rotation of the sample holder prevents the strong lensing (caused by cylindrical holder surface) from occurring. In other embodiments, other materials and shapes can be used for block 250 that approximates the permittivity of the material being measured and achieves improved measurements depending upon the application in which it is applied (peanuts, grains, seeds, coffee beans, etc.). In a related embodiment, a rectangular block similar to block 250 is formed with a cavity of desired shape or a cylindrical hole, thereby dispensing with the cylindrical holder 220 if the user desires. In yet another related embodiment, a cylindrical sleeve with a permittivity/dielectric constant in the same range as the material being measured can also be used around cylindrical holder 220, a range for the permittivity/dielectric constant around 2-10.

Figure 6:
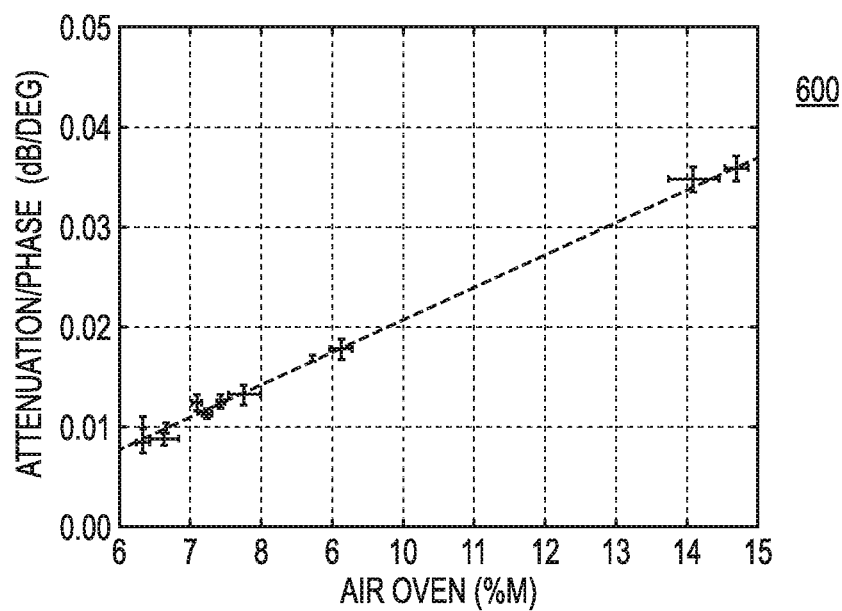
FIG. 6 is a graph that illustrates attenuation/phase ratio for a cylinder with matching block geometry configuration for a moisture meter in accordance with the invention.

Referring now to FIG. 6, there is shown a graph that illustrates the attenuation/phase ratio once the rectangular block 250 is used with cylindrical holder 220. In this example, the Attenuation/Phase ratio is shown as a function of the peanut moisture for the matching block geometry. Note that the sensitivity of the embodiment in FIG. 5 is considerably more than what was seen on FIG. 4B. In addition, the standard deviation in the measurement is around 50-60% of what was measured with the original rectangular sample holder 20.

Figure 8:
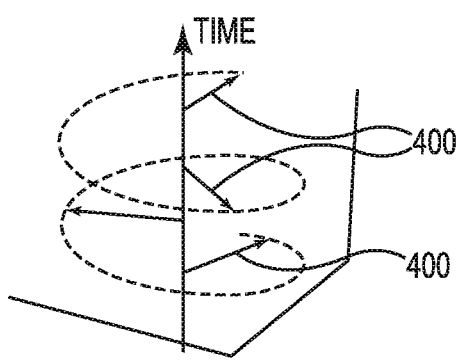
FIG. 8 is a graph that illustrates circular polarization in accordance with the invention.

Referring now to FIG. 8, in a related embodiment, another solution for sensing or detecting moisture is to use circular polarization, with arrows 400 showing the electric field direction at a point in space as a function of time formed by the transmitting and the receiving antennas of the metering arrangement. An advantage to using circular polarized signals is the reduction of variation in the moisture measurements that is caused by the differing orientation of the many particles, in this case peanuts, in the sample material to be measured. In the original design, the antennas are operated with linear polarization (either horizontal or vertical), but they can also be operated in the elliptical polarization mode. There will be a variation coming from the percent alignment of the long axis of the peanuts with the polarization of the electric field. Thus, if two different peanut loading schemes cause the peanut alignment to change, then they could read or detect slightly different levels of moisture. Hence, to address this issue of contradictory measurements of moisture levels, the transmitting and receiving antennas are operated with the circular polarization configuration shown in FIG. 8. This causes the polarization of the microwave to rotate in a circle in a plane normal to the direction of propagation, hence traveling in a corkscrew fashion from the transmitting antenna through the sampled material to the receiving antenna and providing more complete coverage over the entire sampled material. Thus, combining this approach with the cylinder shaped sample holder and the rotation approach of FIG. 2 and FIG. 5, the fraction of the time that the electric field aligns with a peanut will approximately be the same for every peanut (or any other grain or kernel used with this approach), thereby eliminating the contradictory moisture measurements.

The following patents and publications are herein incorporated by reference in their entireties: U.S. Pat. Nos. 4,257,001; 6,147,503; 6,691,563; 8,629,681.

The foregoing specific embodiments of the present invention as set forth in the specification herein are for illustrative purposes only. Various deviations and modifications may be made within the spirit and scope of the invention without departing from the main theme thereof.

What is claimed is:

1. A method of measuring moisture in a sample material located within a material sample holder assembly by measuring attenuation and phase changes in a signal transmitted through the sample of material being measured, the method comprising:

providing an inner cylindrical holder member disposed within an outer holder member, the inner cylindrical holder member having a longitudinal axis along a length of the cylindrical holder and configured to be rotated axially about the longitudinal axis within the outer holder member, wherein the outer holder member is configured from a material that approximates a permittivity of the sample material being measured within the sample holder assembly;

rotating axially the inner cylindrical holder within the outer holder member;

transmitting from a side of the material sample holder assembly a polarized microwave signal; and receiving from an opposite side of the material sample holder assembly the polarized microwave signal transmitted through the material sample holder assembly.

2. The method of claim 1, wherein a mode of polarization of the microwave signal is circular.

3. The method of claim 1, further comprising the step of providing antennas to transmit and receive the polarized signal, each of the antennas with a height substantially similar to a height of the cylindrically shaped sample holder.

4. The method of claim 1, further comprising the step of providing the outer holder substantially in the shape of a block to support the cylindrically shaped holder between a transmitting antenna and a receiving antenna.

5. The method of claim 1, wherein a mode of polarization is linear in either the horizontal or vertical direction.

6. The method of claim 1, wherein a mode of polarization is elliptical.

7. The method of claim 1, further comprising selecting the permittivity of the inner and outer holder members to be in a midrange of a percent moisture content of the individual particles of the sampled material.

8. A method of measuring moisture in a sample material located within a material sample holder assembly by measuring attenuation and phase changes in a signal transmitted through the sample of material being measured, the method comprising:

configuring the material sample holder assembly with a holder member having a longitudinal axis along a length of the holder member and an outer holder member disposed outside and about the holder member, wherein the outer holder member is configured from a material that approximates a permittivity of the sample material being measured within the material sample holder assembly;

transmitting from a side of the material sample holder assembly a polarized microwave signal; and receiving from an opposite side of the material sample holder assembly the microwave signal transmitted through the material sample holder assembly.

9. The method of claim 8, further comprising the step of axially rotating the holder member.

10. The method of claim 9, wherein the holder member is configured as a substantially cylindrical holder member capable of rotating axially within the outer holder member.

11. The method of claim 8, wherein a mode of polarization is selected from a group consisting of circular, elliptical, linear in a horizontal direction and linear in a vertical direction.

12. The method of claim 8, wherein the holder member has one of an oval, elliptical or cylindrical cross section.

13. The method of claim 12, wherein the holder member is configured to have a permittivity selected to be in a midrange of a percent moisture content of the individual particles of the sampled material.

14. A method of measuring moisture in a sample material located within a material sample holder assembly by measuring attenuation and phase changes in a signal transmitted through the sample of material being measured, the method comprising:

configuring the material sample holder assembly to approximate a permittivity of the sample material being measured within the material sample holder assembly;

transmitting from a side of the material sample holder assembly a polarized microwave signal in at least one of a circular, linear and elliptical polarization mode to reduce differences in moisture measurements due to orientation of a particle in the sampled material located in the sample holder assembly; and receiving from an opposite side of the material sample holder assembly the polarized microwave signal transmitted through the material sample holder assembly.

15. The method of claim 14, further comprising the step axially rotating the material holder assembly about a longitudinal axis of a cavity of the material holder assembly.

16. The method of claim 15 further comprising the step of providing an inner holder member configured to hold the sampled.

17. The method of claim 16, wherein the inner holder member is substantially cylindrical in shape and is comprised of material having a permittivity selected to be in a midrange of a percent moisture content of the individual particles of the sampled material.

18. The method of claim 14, wherein the permittivity of the material sample holder assembly is selected to be in a midrange of a percent moisture content of the individual particles of the sampled material.

19. The method of claim 16, wherein the inner holder member has an oval or elliptical cross section, the inner holder member configured to have a permittivity selected to be in a midrange of a percent moisture content of the individual particles of the sampled material.

* * * * *